(12) United States Patent
Friis et al.

(10) Patent No.: US 8,409,610 B2
(45) Date of Patent: Apr. 2, 2013

(54) WOUND CARE DEVICE

(75) Inventors: Gitte Juel Friis, Hoersholm (DK); Truels Sterm Larsen, Frederiksberg C (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/230,479

(22) Filed: Sep. 12, 2011

(65) Prior Publication Data
US 2012/0064146 A1    Mar. 15, 2012

Related U.S. Application Data

(63) Continuation of application No. 10/560,181, filed as application No. PCT/DK2004/000427 on Jun. 18, 2004, now Pat. No. 8,039,017.

(30) Foreign Application Priority Data

Jun. 19, 2003   (DK) ................................ 2003 00920

(51) Int. Cl.
| | |
|---|---|
| *A61K 9/70* | (2006.01) |
| *A61K 47/32* | (2006.01) |
| *A61K 47/34* | (2006.01) |
| *A61K 47/38* | (2006.01) |
| *A61K 47/06* | (2006.01) |
| *A61K 31/192* | (2006.01) |
| *A61K 47/36* | (2006.01) |
| *A61P 17/02* | (2006.01) |
| *A61P 29/00* | (2006.01) |

(52) U.S. Cl. ..................... 424/449; 514/570; 514/772.5; 514/772.4; 514/772.3; 514/777; 514/781; 514/772

(58) Field of Classification Search .................. None
See application file for complete search history.

(56) References Cited

U.S. PATENT DOCUMENTS

| | | | |
|---|---|---|---|
| 4,231,369 A | 11/1980 | Sørensen et al. | |
| 4,367,732 A | 1/1983 | Poulsen et al. | |
| 5,051,259 A | 9/1991 | Olsen et al. | |
| 5,643,187 A | 7/1997 | Næstoft et al. | |
| 5,714,225 A | 2/1998 | Hansen et al. | |
| 5,719,197 A | 2/1998 | Kanios et al. | |
| 5,759,563 A * | 6/1998 | Yewey et al. ................. | 424/426 |
| 5,792,469 A | 8/1998 | Tipton et al. | |
| 5,910,489 A | 6/1999 | Falk et al. | |
| 5,993,849 A | 11/1999 | Assmus et al. | |
| 6,048,850 A | 4/2000 | Young et al. | |
| 6,117,437 A | 9/2000 | Roreger | |
| 6,190,689 B1 | 2/2001 | Hoffman et al. | |
| 6,190,690 B1 | 2/2001 | Park et al. | |
| 6,245,357 B1 | 6/2001 | Edgren et al. ................. | 424/473 |
| 6,312,713 B1 | 11/2001 | Korol et al. | |
| 6,500,539 B1 | 12/2002 | Chen et al. | |
| 6,676,962 B1 | 1/2004 | Müller | |
| 6,713,083 B1 | 3/2004 | McGregor et al. | |
| 8,039,017 B2 * | 10/2011 | Friis et al. ..................... | 424/445 |
| 2003/0170308 A1 * | 9/2003 | Cleary et al. .................. | 424/486 |
| 2005/0074486 A1 | 4/2005 | Juel-Friis et al. | |
| 2005/0276842 A1 | 12/2005 | Zhang et al. .................. | 424/448 |
| 2007/0009583 A1 | 1/2007 | Qvist ............................ | 424/445 |

FOREIGN PATENT DOCUMENTS

| | | |
|---|---|---|
| EP | 0 808 158 | 11/1997 |
| GB | 2 300 195 | 10/1996 |
| GB | 2 311 027 A | 9/1997 |
| WO | WO 87/05206 | 9/1987 |
| WO | WO 94/23713 | 10/1994 |
| WO | WO 96/23488 | 8/1996 |
| WO | WO 98/22114 | 5/1998 |
| WO | WO 00/02539 | 1/2000 |
| WO | WO 00/07574 | 2/2000 |
| WO | WO 01/15750  * | 3/2001 |
| WO | WO 01/80797 A1 | 11/2001 |
| WO | WO 03/055536 A1 | 7/2003 |

OTHER PUBLICATIONS

"Fourth Grade Math", pp. 1-4 found at: http://www1.center.k12.mo.us/edtech/edm/4/htm and http://www.aaastudy.com/dec44cx2.htm, Sep. 2010.

* cited by examiner

*Primary Examiner* — Shanon A Foley
(74) *Attorney, Agent, or Firm* — Jacobson Holman PLLC

(57) ABSTRACT

A wound care device for local treatment of pain in a wound, said device comprising an active pain relieving composition, the device being constructed in such a manner that the pain killing agent is released to the wound in such a way that substantially no effective systemic plasma concentration of the pain killing agent can be found and wherein a majority of said pain killing agent is in direct contact with the wound.

19 Claims, 4 Drawing Sheets

WOUND CARE DEVICE

This is a CONTINUATION OF U.S. application Ser. No. 10/560,181 filed Dec. 9, 2005 now U.S. Pat. No. 8,039,017, which is a nationalization of PCT/DK2004/000427 filed Jun. 18, 2004 and published in English, which claims priority from PA 2003/00920, filed in Denmark on Jun. 19, 2004, the disclosures of each of which are hereby incorporated by reference.

BACKGROUND OF THE INVENTION

1. Field of the Invention

This invention relates to wound care devices comprising an active pain-relieving agent for local pain relief in an open wound setting and a method of treating pain in such wounds.

It is widely recognized that wound pain is one of the major problems associated with wounds or ulcers. Wounds are by definition divided into two categories: Acute and chronic wounds. Acute wounds may be wounds such as burns and surgical wounds, while chronic wounds may be in the form of pressure sores, leg ulcers and diabetic ulcers. Pain can be associated with both chronic and acute wounds although the influence on well being of a patient will be more pronounced when the wound is chronic.

Pain can be divided into three categories: Acute pain, non-malignant pain and cancer pain. Wound pain will often be either acute or non-malignant dependent on the character of the actual wound and whether the wound is being manipulated or not e.g. during a dressing change. Furthermore, the pain will in general have nociceptive or neurogen origin.

The actual kind of wound pain can be divided into three classes:
  Non-cyclic acute wound pain, which may occur during for instance at debridement of necrotic tissue in a wound or removal of drainage.
  Cyclic acute wound pain, which may occur during for instance dressing changes or in some cases debridement.
  Chronic wound pain, which is a persistent pain that occur even without manipulation of the involved skin or tissue, i.e. pain between dressing changes.

In the following we will primarily address relief of the persistent pain or the chronic pain associated with wounds between dressing changes. However, treatments suitable for this purpose may also be able to relieve pain during dressing change and debridement as described below.

Pain in itself is of course a major discomfort for the patient and will therefore affect patient's quality of life. In addition, pain stimulates catecholamine release and as a result of that local vasoconstriction arises and a reduced oxygen supply to a cutaneous wound will occur. This may affect wound healing and resistance to infection of the wound. Furthermore, wound healing may also be delayed due to the general influence pain may have on the patient, such as loss of appetite, less mobility, worse overall condition and lack of enthusiasm. However, the possible effect of pain on wound healing has not been proven in the literature and is therefore speculative. In contrast, it is well recognized that pain has an impact on the health related quality of life (HRQoL) for patients.

Wound pain has proven to be decreased by modern moist wound healing principles. Moist wound healing dressings keep the environment under the dressing moist but are at the same time capable of absorbing considerable amounts of exudate from the wound, in order to protect the periulcer skin and to avoid leakage. During the wear time of a moist wound healing dressing, tissue and nerve endings remain moist. Such dressings, e.g. hydrocolloid dressings will be soothing and less painful than traditional dry gauze dressings during application and in situ. Debridement will often also be less painful as the wound bed will be kept in a moist condition and thus no painful drying out is seen.

Although moist wound healing has been proven to improve healing rates, relieve pain in situ, prevent the wound bed from drying out, decrease the discomfort with wound debridement and overall improve the quality of life for the patient, added benefits in terms of a more direct way of addressing the local wound pain between dressing changes associated with wounds are still needed.

2. Description of the Related Art

It is well known in the art to incorporate analgesics or anaesthetics into topical products for treatment of pain or to produce anaesthesia in intact skin surfaces or systemically in the body. These products may be in the form of trans-dermal dressings or patches, creams, gels or ointments. In order to enhance the rate at which the drug passes through the skin to reach the systemic circulation from e.g. the trans-dermal patch or to achieve an appropriate formulation for intact skin surfaces it is often desirable or even necessary to incorporate other components. These components will interfere with an open wound setting in terms of producing possible irritation, sensibilisation or even toxicological effects in the open wound setting and to the often very fragile periulcer skin around the open wound.

In International Patent Application No. WO 94/23713 is disclosed a trans-dermal anti-inflammatory composition. The compositions may be used for topical and trans-dermal application, such as ointments and dressings and the anti-inflammatory composition is preferably NSAIDs (non-steroid anti-inflammatory drugs).

However, delivering drugs to intact healthy skin and to the systemic circulation is very different from delivering drugs locally to open wounds or damaged skin. The skin provides an effective barrier between the drug and the underlying tissue and blood circulation in trans-dermal delivery, and therefore, the drug has to be formulated in such a way that it is capable of overcoming this barrier. Also the concentration of the drug in the trans-dermal formulation has to be higher in order to overcome the skin barrier and reach the systemic circulation in a plasma concentration high enough for systemic effect. A wound is provided with little or no barrier, and furthermore, the wound will often exudate and may be contaminated. The exudate comprises complex wound components such as enzymes, proteins or other plasma components. The barrier for the release of the drug for local use in an open wound will be the medical device and not the intact skin.

A trans-dermal patch or a topical cream or ointment will not be a part of an open wound handling solution and neither will the adhesive nor the other components of the patch be designed for use on an open wound or for contact with the very fragile skin surroundings. Also the drug concentration in a trans-dermal system or a topical ointment, gel or cream may be too high to be used in an open wound where no absorption barrier is seen. Furthermore, additives such as penetration enhancers comprised in the creams, gels or ointments or trans-dermal patches will make them unsuitable for use in an open wound, as these additives often are too aggressive or even toxic for introducing directly into an open wound.

Most wound care products are prepared without such additives as these additives may interfere with the wound healing and influence the well being of the patient.

A controlled release of drugs is often desired both in trans-dermal delivery and open wound treatment. However, the release mechanisms may be quite different in the two systems. In a trans-dermal device such as a patch, cream, ointment or gel, the skin barrier may serve as the controlling release layer. The additives may further control the release. In a wound care device, the release may be controlled in other ways, e.g. by the amount of exudate from the wound, or by using controlled release matrices.

Analgesics in a broad term can relieve pain in open wounds without seriously interfering with the sense perception. In contrast, anaesthetics interfere with sense perception when applied locally, and can result in loss of consciousness when used centrally. Loss of sense perception in a wound and surroundings is considered to be irrationally and inconvenient since the patient loose the ability to feel possible injury and change in the wound. Therefore it may be preferred to use analgesics in order to relieve wound pain over a longer period.

In U.S. Pat. No. 6,312,713 is disclosed a thin-layered dressing for surface wounds which gradually releases drugs, such as analgesics. The drug is incorporated in a hydrophilic polymeric matrix and may be used topically. The reference is silent with respect to the amount of active agent incorporated therein.

In U.S. Pat. No. 6,048,850 is disclosed a method of selectively inhibiting PGHS-2 in a human host. The reference is silent with respect to local wound treatment.

U.S. Pat. No. 6,190,689 discloses a trans-dermal device comprising a hot-melt adhesive with an incorporated substance. The use of pain relieving agents in the treatment of wounds is mentioned, but the reference is silent with respect to any details or examples to this subject.

In International Patent Application No. WO 00/07574 is disclosed medicinal products with retarded pharmacological activity. The products are primarily intended for use in catheters, though use in wound care devices is mentioned.

In EP 808 158 B1 a single-dose pharmaceutical form for delivery of active substances to a wound is described. It is in the form of a film-like flexible substrate. The reference is silent with respect to the use of pain relieving substances.

Thus, there is still a need for a medical device addressing superior wound management as well as local pain relief in terms of addition of analgesic compounds. Such a wound care device is achieved by the present invention combining a flexible use with the pharmacological effects of a pain relieving agent, that supply pain relief locally to a wound and nearby surroundings but not systemically i.e. in the body.

SUMMARY OF THE INVENTION

One object of the present inventions is to provide a simple wound care device being capable of releasing a pain-killing agent to a wound.

Another object of the invention is to provide a pain relieving wound care device with a local but not systemic effect.

Yet another object of the invention is to provide a pain relieving wound care device wherein the side effects are reduced or eliminated.

A further object of the present invention is to provide a wound care device being capable of releasing a pain-killing agent to a wound substantially independent of the amount of exudates.

A further object of the present invention is to provide a wound care device being capable of releasing a pain-killing agent to a wound even when only low levels of exudates is present.

A still further object of the invention is to provide a wound care device, which is capable of releasing a majority of the pain-killing agent present in the device during the first 24 hours of application.

The present invention relates to a wound care device for treatment of pain in a wound comprising an active pain relieving composition.

BRIEF DESCRIPTION OF THE DRAWINGS

The invention is further described in the drawings wherein.

DETAILED DESCRIPTION OF THE PRESENT INVENTION

Figure 1:
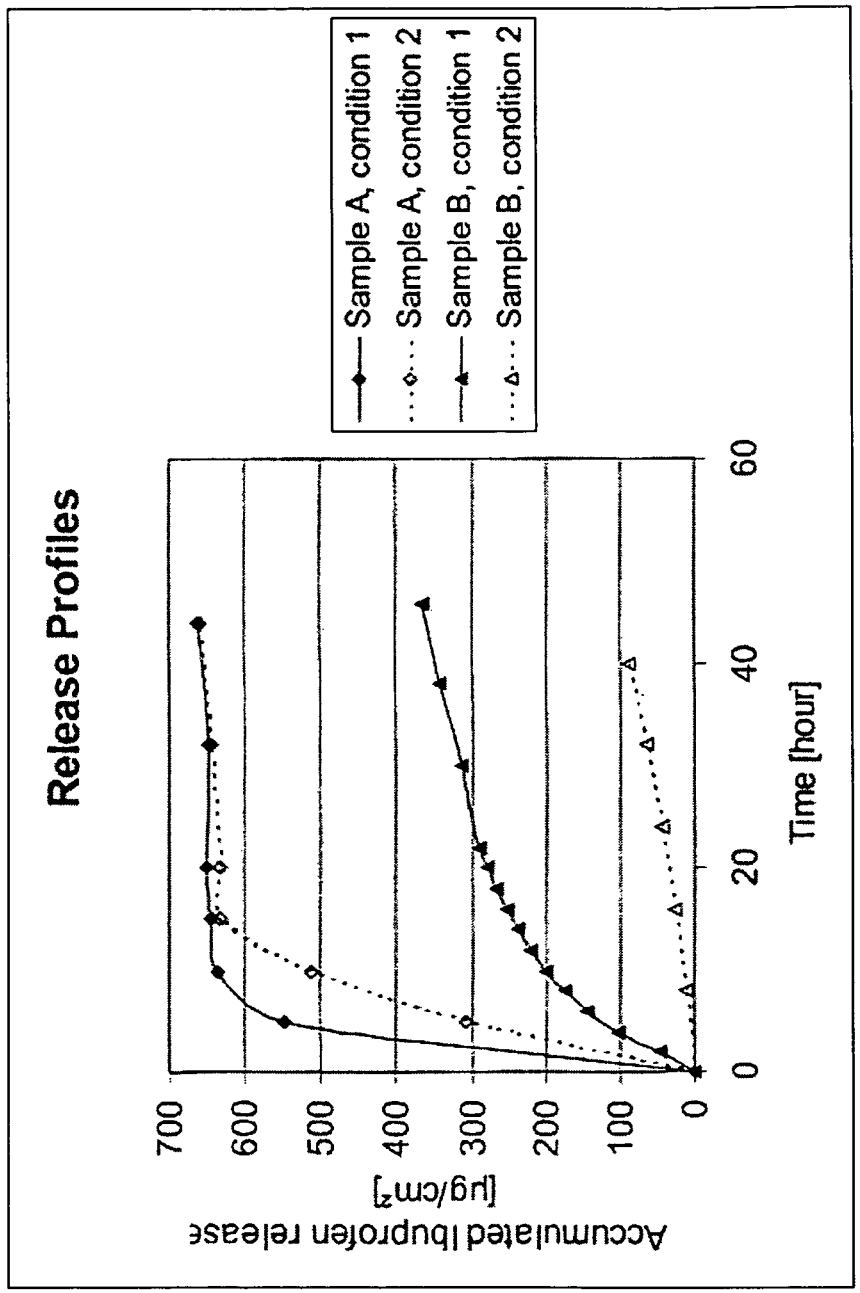
FIG. 1 shows release profiles of a device of the invention compared to a foam dressing.

It is widely held that pain-killing agents, such as anti-inflammatory agents, e.g. NSAIDS, are unsuitable for use in open wound settings. These agents are primarily used for treatment of systemic diseases, not for local treatment. It is further believed that the compositions may cause local irritation, as well as it has been recommended to avoid use of such compositions in open wounds.

It has surprisingly been found that it is possible to incorporate a pain-killing agent in a wound care device; thereby achieving a local pain-relieving effect in an open wound. Even though the pain-killing agent is in direct contact with the wound, no local side effects have been seen and the plasma concentrations, if any, of the agent were below the concentrations for systemic effect.

The device according to the present invention is primarily intended for use as local pain relief. When a systemic effect of the pain-relieving agent is desired e.g. when providing pain relief against rheumatoid arthritis, muscle pain or headaches, orally ingested analgesics may be preferred. The pain relieving composition of the device of the invention may be applied to damaged skin locally and directly onto an open wound without interfering with the wound healing.

The invention relates to a wound care device for local treatment of pain in a wound, said device comprising an active pain relieving composition, the device being constructed in such a manner that the pain killing agent is released to the wound in such a way that substantially no effective systemic plasma concentration of the pain killing agent can be found and wherein a majority of said pain killing agent is in direct contact with the wound.

The invention further relates to a wound care device for local treatment of pain in a wound, said device comprising an active pain relieving composition, said composition is a pain killing agent, wherein the amount of pain killing agent in the device is below the daily unit dose for systemic treatment and wherein a majority of said pain killing agent is in direct contact with the wound.

The pain-killing agent may be an anti-inflammatory pain-killing agent.

By providing a release of pain-killing agent being below the daily unit dose for systemic treatment and/or causing substantially no effective systemic plasma concentration the risk of side effects may be reduced or even eliminated.

It has surprisingly been shown that by establishing direct contact between a majority of the pain-killing agent and the wound, a number of advantages are achieved. The amount of pain-killing agent may be reduced and the likelihood that a substantial portion of the pain-killing agent incorporated actually reaches the wound is improved. Furthermore, the direct contact to the wound facilitates the release.

The direct contact may be obtained by providing the pain-killing agent on the wound-facing surface of the device or by incorporating the agent in a relatively thin wound-contacting layer.

The device of the present invention may be preferably have a thickness of less than 1.5 mm, more preferred less than 1.0 mm, even more preferred less than 0.7 mm and most preferred less than 0.6 mm.

In an especially preferred embodiment of the invention the device has a thickness of 0.5 mm.

The device may exhibit non-stick properties with regards to the wound. These properties may be obtained by selecting a material with this inherent property or by coating the alternatively selected material with a non-stick agent.

Preferably the device of the invention is in the form of a sheet-like layer. This layer may be prepared from any suitable material, such as a web, a net, a knit, a woven or a non-woven fabric, a permeable or perforated film or a foam, or a hydrogel provided that the material exhibits a suitable permeability for wound exudates.

Most preferably the device of the invention is in the form of an open fabric. The fabric may be coated or impregnated with a composition comprising the pain-killing agent. In a preferred embodiment of the invention the composition further comprises a non-stick agent, such as petrolatum. While impregnating a sheet-like layer, such as an open fabric, with such composition, a majority of the pain-killing agent will still be in direct contact with or immediately available for the wound, due to the open structure of the layer.

By the phrase "a majority of" is meant that the main part of the present pain-killing agent is in contact with the wound. By direct contact it is understood that the active agent is positioned next to the wound. In this way the pain-killing agent does not need to migrate through a significant amount of dressing material in order to reach the wound. In a device comprising e.g. a relatively thick foam layer wherein the pain-killing agent is incorporated, only a minor portion of the agent will be immediately available for the wound. Compared to this the present invention provides immediate contact between a majority of the pain-killing agent and the wound by having the pain-killing agent positioned in a relatively thin layer next to the wound.

Depending on the amount of wound exudates the sheet-like device may be used alone or in combination with a secondary dressing having wound exudate-handling means. By having the ability to combine the sheet-like device with any type of secondary dressing a higher flexibility in the wound treatment is achieved.

The device of the present invention may comprise any material or composition of materials that dissolves, swells or allows water diffusion upon contact with water or water based solutions. The device may comprise one or more components selected from the group of PVP, PVA, polylactic acids, polysaccharides such as carboxy methyl cellulose (CMC), hydroxymethyl cellulose, chitosan, alginate, or polyacrylic acids, methacrylates, silicones, styrene-isoprene-styrene mixtures, Vaseline, glycols such as PEG or PEG/PPG mixtures or polyurethane. The material may be hydrophobic or hydrophilic or a combination thereof.

It is preferred that the device of the present invention has a maximum absorption of 0.2 g/cm$^2$, more preferred 0.1 g/cm2, even more preferred 0.075 g/cm$^2$ and most preferred 0.05 g/cm$^2$ or less. The device may preferably be considered as a low- or substantially non-absorbent device as the absorbency is not the main issue of the present invention. In fact, a low absorbency of the device may be desired in order to promote moist wound healing without having this as a primary purpose. Furthermore, the absorbent material may serve to control and distribute the moisture as well as provide non-stick features for the device. The absorbent material may be selected from the group of absorbing foams, hydrogels, or pastes, hydro-sheets or be in the form of hydrocolloids, polysaccharides, such as CMC and/or alginates.

In one embodiment of the invention the device is substantially non-absorbent.

Typically, the release of active agents in wound care devices known in the art is dependent of the amount of wound exudates. However, it may be desirable to control the release being less dependant on the amount of wound exudates.

In different healing phases, wounds will produce different amounts of exudate dependent on the type of wound. Wounds with less exudate can also be painful and thus a wound care device designed to address this is needed. If the release is dependent on the amount of exudate, a simple solution will be to increase the amount of pain relieving substance in the device. However, if the wound is highly exudating the need will be the opposite. Further, it is difficult in a clinical situation to evaluate the actual level of exudate when choosing a specific local pain relieving wound care device. Therefore it may be desired to have a release system that is substantially independent of the amount of wound exudate.

In a preferred embodiment of the present invention the release of the pain killing agent is substantially independent of the amount of wound exudates.

It has surprisingly been shown that the release of pain-killing agent in the device of the invention may be substantially independent of the amount of wound exudates present. By the phrase "substantially independent" is understood that a certain initial amount of moisture has to be present in order to achieve moist wound healing and for initiation of the release process, but amounts of moisture exceeding this initial amount will have very little or no influence to the degree of release of pain-killing agent. When a certain initial amount of moisture is added to the device, a release of pain-killing agent begins. This release will be less affected by the amount of moisture/wound exudates if this is increased. The initial amount of moisture may be the moisture that the device needs to be wetted or in some cases saturated. In the case of a dry wound, a portion of saline water may be added to the wound before application of the device of the invention.

In one embodiment of the invention the amount of pain killing agent is less than 75% of the systemic daily unit dose for systemic treatment using the agent.

In another embodiment of the invention the amount of pain killing agent is less than 50% of the systemic daily unit dose for systemic treatment using the agent.

It may be preferred that the amount of pain killing agent is less than 25% of the systemic daily unit dose for systemic treatment using the agent.

It is even more preferred that the amount of pain killing agent is less than 10% of the systemic daily unit dose for systemic treatment using the agent.

In one embodiment of the invention the amount of pain killing agent is less than 5% of the systemic daily unit dose for systemic treatment using the agent.

By the phrase "systemic daily unit dose for systemic treatment for a pain killing agent" is meant the daily dose for achieving a systemic pain reliving effect, i.e. achieving a desired plasma concentration.

When referring to an amount of pain-killing agent below the daily unit dose for systemic treatment, it is understood that the amount of pain-killing agent in a device according to the present invention is below the lowest value recommended for the specific pain-killing agent.

In Table 1 are shown examples of systemic or topical daily unit doses of various pain killing agents. Examples of systemic daily unit doses for normally recommended use for adults are shown below.

TABLE 1

| Drug | Recommended systemic daily unit dose |
|---|---|
| Naproxen | 500-1000 mg |
| Ketoprofen | 100-300 mg |
| Piroxicam | 10-20 mg |
| Ibuprofen | 600-1200 mg |
| Celecoxib | 200-400 mg |
| Acetylsaliclylic acid | 2-4 g |
| Indomethacin | 50-150 mg |
| Acetaminophen | 1.5-4 g |
| Diclofenac | 75-150 mg |
| Morphine | 25-30 mg |
| Ketobemidon | 15-30 mg |
| Codein | 30-60 mg |

The analgesics in the device of the invention may be released locally to the wound. Preferably, the release of the pain relieving composition is so low that no systemic effect is seen. Thus, the concentration of analgesics in the device of the invention may be so low that substantially no effective systemic plasma concentration can be found. This will reduce or even eliminate the possible systemic side effects of the analgesics, and at the same time provide the patient with maximum safety, as oral doses or topical doses on intact skin can be taken at the same time. Thus, the device renders it possible to ingest additional medication, if needed, orally or topically of the same type as in the wound care device, without the risk of overdosing. Furthermore, side effects are lowered and compliance will be better as well as the HRQoL.

For different analgesics, minimum plasma concentration for obtaining systemic effect is reported to be as follows given as examples: Acetylsalicylic acid: 270 µg/ml; Ketoprofen: 3 µg/ml; Ibuprofen: 10 µg/ml; Piroxicam: 1 µg/ml. Thus, a wound care device for treatment of pain in a wound releasing analgesics locally to a wound site may be designed in such a way that the plasma concentration is under the lowest value for systemic effect in the body.

This is also true for other anti-inflammatory pain reliving compositions being suitable for incorporation into medical devices for local treatment of wound pain in open wounds.

Prostaglandins, leukotrienes, and thromboxanes are key inflammatory mediators produced from arachidonic acid. Inhibition of the synthesis of these mediators is the target of the most highly prevalent class of anti-inflammatory drugs, the NSAIDs. Inflammatory mediators will stimulate pain nociceptors and as a result pain is produced.

Pain impulses in skin tissue arise from pain receptors in the skin and deeper structures. The intensity of the pain increases when the number of receptors activated and the frequency of impulses increase. The perception of pain in e.g. peripheral tissue such as the skin begins with stimulation of nerve fibres called nociceptors. In a process called transduction, a nociceptive stimulus makes nociceptor membranes permeable to sodium ions. In a second process known as transmission, the influx of sodium ions sends a signal to the dorsal horn of the spinal cord. In a third process, modulation, systems that inhibit and facilitate pain act on the generated signals. Finally in the perception process a factor called plasticity, which is based in part on prior experienced pain, determines how intensely the pain is perceived. Pain is therefore also subjective. It has both a psychological and physiological component. Acute, and social, cultural and psychological factors affect it. The feeling of pain is protective in situations where it alerts the body of actual or potential damage. Beyond these situations its function is less clear.

Inflammatory pain is believed to be important for the actually feeling of chronic or persistent wound pain. It is believed that tissue injury as e.g. seen in chronic wounds triggers the release of multiple inflammatory mediators that themselves, alter nociceptor function. The level of inflammation is therefore elevated and may be lowered by addition of anti-inflammatory drugs locally to the wound that would lead to pain relief.

Preferably the pain relieving composition comprises an anti-inflammatory painkilling agent that blocks the production of inflammatory mediators produced from arachidonic acid.

More preferably the pain-killing agent is a NSAID (non-steroid anti-inflammatory drug). NSAIDs generally have analgesics and antipyretic properties along with their anti-inflammatory capabilities. Anti-inflammatory pain killing agents interact with enzyme targets such as cyclooxygenase-inhibiting NSAIDs. The enzymes PGHS (prostaglandin H synthease), commonly know as COX (cyclooxygenase), is responsible for processing arachidonic acid into inflammatory mediators. COX comes from two isoforms COX 1 and COX 2. COX 1 is produced in a more or less constant level at all times and is involved in forming the prostaglandins that perform several important functions, including protection of the gastric mucosa and support of renal function. Consequently, inhibitors of COX 1 may interfere with the gastric mucosa and renal function. COX 2, which is inducible, is expressed after tissue injury and promotes inflammation. Thus, selective inhibition of COX-2, with sparing of COX 1 activity, should be expected to block inflammation without gastric and renal side effects upon oral administration. However, use of COX 1 locally in an open wound setting will not produce any systemic side effects. Classical NSAIDs acts on both COX 1 and COX 2 whereas newer drugs work selectively on COX 2.

Thus, in one embodiment of the invention the pain relieving composition may be capable of inhibiting mediators responsible for processing arachidonic acid into inflammatory mediators.

In preferred embodiment of the invention the pain relieving composition may be capable of inhibiting COX 1 and COX 2.

In one embodiment of the invention the pain relieving composition may be capable of specifically inhibiting COX 2. The pain relieving composition may comprise one or more compounds chosen from the group of anti-inflammatory compositions such as Phenylpropionic acids, Phenelacetic acids, Indoleacetic acids, Pyrroleacetic acids, N-Phenylacetic acids, Salicylates, Enolic acids, Phenols, Non-acids or Cox-ibs.

Examples of such compounds for the pain relieving composition may be: Propionic acid derivatives such as Naproxen, Ibuprofen, Ketoprofen, Fenoprofen, Flurbiprofen Dexibuprofen or Tiaprofenic acid, Acetic acid derivatives such as Diclofenac, Alclofenac, Fenclofenac, Etodolac, Aceclofenac, Sulindac or Indomethacin, Pyrroleacetic acids such as Ketorolac or Tolmetin, N-Phenylacetic acids such as Mefenamic acid, Salicylates such as Acetyl salicylic acid (Aspirin), Salicylic acid or Diffunisal, Pyrazolon derivatives such as Phenylbutazone, Oxicam derivatives such as Piroxicam, Tenooxicam, Meloxicam or Lornoxicam, Enolic acid derivatives Aminopyrene or antipyrene, Phenols such as Acetaminophen or Phenacetin, Non-acid derivatives Nabumeton, Coxib derivatives such as Celecoxib or Rofecoxib.

Compounds inhibiting COX 2 specifically may be Coxib derivatives such as Celecoxib or Rofecoxib.

In one embodiment of the invention the pain relieving composition is Ibuprofen.

In another embodiment of the invention the pain relieving composition is Ketoprofen.

The pain relieving composition may be incorporated as particles, coated particles or diluted in constituent phases of the medical device or distributed in an aiding agent therein. In one embodiment of the invention the pain-killing agent is in the form of a coated layer.

The particles may be mixed with one or more of the constituents of the wound care device, such as the particles may be incorporated into an adhesive, an absorbent layer or they may be incorporated in a film.

The pain relieving composition may be dissolved or suspended in one or more of the constituents of the wound care device or alternatively in one or more constituents acting as precursor material for the constituent.

In one embodiment of the invention the particles may be dissolved in an aiding vehicle in the form of a liquid or solid and may appear as a discrete phase in one or more of the components of the device, e.g. a water insoluble composition may be incorporated into a hydrophobic vehicle or vice versa.

By having a direct contact to the wound the amount of pain-killing agent in the device may be minimized. This may be important if the pain-killing agent is expensive, or in the case that the pain-killing agent may be toxic in high doses. An pain-killing agent being incorporated into a wound care device as known in the art, e.g. a foam dressing, may have some of the pain-killing agent trapped in the foam and thus never released. Another situation could be that the entire amount pain-killing agent was released, even though it was expected that some of it would remain in the dressing, and thus an overdose of pain-killing agent may be the undesired result. By the device of the present invention it is easier to control the release of the pain-killing agent due to the direct contact to the wound.

In the device of the present invention at least 50% w/w of the pain-killing agent may be released during the first 24 hours, more preferred 12 hours and most preferred 6 hours after application, and/or at least 75% w/w of the pain-killing agent may be released during the first 24 hours, more preferred 12 hours and most preferred 6 hours after application and/or at least 90% w/w of the pain-killing agent may be released during the first 24 hours, more preferred 12 hours and most preferred 6 hours after application.

By releasing a majority or substantially the entire amount of pain-killing agent shortly after application of the device to the wound, an instant pain relief is achieved. Furthermore, the device may be used as a wound contact layer with a burst-release effect. Combining such burst release layer with a secondary dressing, such as an absorbent dressing also with pain-killing agent incorporated, and capable of a slow release, the contact layer will provide an effective dose of agent in a short time, while the secondary dressing will provide a prolonged release in order to improve wear time.

The pain relieving effect of the device according to the invention is over time originated from release of the pain-killing agent to the wound. When studying a dressing that has been applied over an open wound for a period, the pain killing agent diminish or disappear in the area directly over the wound due to a release to the wound, while a negligible amount will be released in the area over the periulcer skin.

In one embodiment of the invention the pain-relieving component may be in the form of coated particles with controlled release properties. The coating may be any suitable coating known in the art of release systems providing the particles with the desired release properties.

Preferably, the device of the invention is in the form of a wound dressing, or a part of a wound dressing, such as a wound-contacting layer. The device or part of the device is preferably soft, non-sticking to the wound bed and easily removable.

The dressing may be in the form of a single unit or a layered product and may be used as a primary dressing together with a secondary dressing. A primary dressing is the part that is in direct contact with the wound bed.

The secondary dressing may comprise an absorbent element. It may in itself show adhesive properties or it may not show adhesive properties and it will then typically be secured to the desired site using conventional means such as a cover dressing.

The device of the invention may comprise an adhesive.

The device of the invention may comprise a skin-contacting surface comprising an area showing a skin friendly adhesive.

Such a wound care device may suitably be a dressing comprising a substantially water-impervious layer or film and a skin-friendly adhesive in which an absorbing constituent or element is incorporated.

The skin-friendly adhesive may be any skin-friendly adhesive known per se, e.g. an adhesive comprising hydrocolloids or other moisture absorbing constituents such as the adhesives disclosed in U.S. Pat. Nos. 4,231,369 and in 4,367,732 comprising hydrocolloids. A dressing comprising a separate absorbing element may e.g. be of the type disclosed in U.S. Pat. Nos. 5,051,259 or 5,714,225.

A water impervious layer or film may be of any suitable material known per se for use in the preparation of wound dressings e.g. a foam, a non-woven layer or a polyurethane, polyethylene, polyester or polyamide film. A suitable material for use as a water impervious film is a polyurethane such as the low friction film material is disclosed in U.S. Pat. No. 5,643,187.

In another embodiment of the invention the device may be a wound cavity filler. The cavity filler may e.g. be in the form of fibers, a sheet, a gel or a hydrogel, thin foam or powder.

The device of the invention may further comprise one or more active ingredients besides the pain-killing agent.

The wound care device according to the invention may comprise one or more active ingredients besides the pain-killing agent, e.g. a pharmaceutical medicament. Examples of such pharmaceutical medicaments such as bacteriostatic or bactericidal compounds, e.g. iodine, iodopovidone complexes, chloramine, chlorohexidine, silver salts such as sulphadiazine, silver nitrate, silver acetate, silver lactate, silver sulphate, silver sodium thiosulphate or silver chloride, zinc or salts thereof, metronidazol, sulpha drugs, and penicillin's, tissue-healing enhancing agents, e.g. ROD tripeptides and the like, proteins, amino acids such as taurine, vitamins such ascorbic acid, enzymes for cleansing of wounds, e.g. pepsin, trypsin and the like, proteinase inhibitors or metalloproteinase inhibitors such as Illostat or ethylene diamine tetraacetic acid, cytotoxic agents and proliferation inhibitors for use in for example surgical insertion of the product in cancer tissue and/or other therapeutic agents which optionally may be used for topical application, emollients, retinoids or agents having a cooling effect which is also considered an aspect of the invention.

The active ingredient may also comprise odor controlling or odor reducing material such as charcoal.

The invention further relates to a method of treating pain at a wound site comprising applying to the wound a wound care device comprising an active pain relieving composition, said composition is an anti-inflammatory pain killing agent, wherein the amount of pain killing agent in the device is below the daily unit dose for systemic treatment and wherein a majority of the pain killing agent is brought into direct contact with the wound.

The pain relieving composition may preferably be an anti-inflammatory pain relieving composition, said composition is an anti-inflammatory pain killing agent, wherein the amount of pain killing agent in the device is below the daily unit dose for systemic treatment and wherein the pain killing agent is brought into direct contact with the wound.

When applying a wound care device according to the invention to a wound, the pain relieving composition is brought into direct contact with the wound and will then be released in a fast and efficient manner to the wound bed, whereby pain relief is achieved.

Materials and Methods

EXAMPLE 1

Two samples were prepared and tested as described below.
Sample A
Preparation of a Wound-Contacting Layer
A mixture consisting of:

| Ibuprofen | 2.5% w/w |
|---|---|
| Carboxymethyl cellulose | 15% w/w |
| Vaseline | 82.5% w/w |

Mixture was heated to 60° C. and mixed with an Ultra Turrax™ equipment for 10 minutes at 16000 rpm. The mixture was then applied and impregnated onto a simple net in the form of a polyester gauze. The resulting contact layer has a mean Ibuprofen concentration of approximately 0.5 mg/cm$^2$.
Sample B
Preparation of a Foam Dressing
A polyurethane foam was prepared in the following way:
100 parts w/w Hypol2002 (Dow Chemical Company)
1 part w/w Pluronic 62 (BASF)
100 parts w/w water
1 part w/w Ibuprofen The materials components were mixed together for approximately 15 seconds. The liquid was poured into a mould and allowed to react for 10 minutes. The resuiting foam sheet was dried in an oven at 70° C. for 30 minutes, and then cut into 20×20 cm dressings with a thickness of 4.4 mm. A top film was laminated onto one side of the foam dressing. The foam dressing has a mean Ibuprofen concentration of approximately 0.5 mg/cm$^2$. The device may further be sterilized using beta or gamma radiation.
Method A diffusion test on Franz diffusion cells was established to investigate in vitro simulation of a high and moderate exuding ulcer. Condition 1 represents a high exuding ulcer, whereas condition 2 represents a moderate exuding ulcer.

The Franz diffusion cell comprises a donor compartment and a receptor compartment divided by a release unit. The donor compartment was empty and the receptor compartment was filled with a USP phosphate buffer solution (pH 7.4). The release unit was placed on top of the receptor compartment with a water impermeable rubber outer layer on top that leaves the donor compartment dry.
Condition 1:

For measurement on a flow-through cell, the Franz diffusion cell was used. Sample roundels of 20 mm in diameter were applied onto each cell as described above. The cell had an inner volume of 14 ml. The flow rate was 13.1 micro Liter/minute. Auto sampling was carried out at different adequate times.
Condition 2:

Sample roundels of 20 mm in diameter were applied onto an agar middle layer covering a membrane with a pore size of 0.02 µm. This will diminish the donation of water to the sample. The agar membrane layer was then applied on top of the receptor compartment and the sample was placed on top of this as described above. The results are shown in FIG. 1.

The results show clearly that the difference in release measurement i.e. condition type has a large impact on Sample B. In Sample B, the release of the pain-killing agent is strongly influenced by the amount of exudates, while the release from the dressings of Sample A is only slightly impacted by the exudate.

Figure 2:
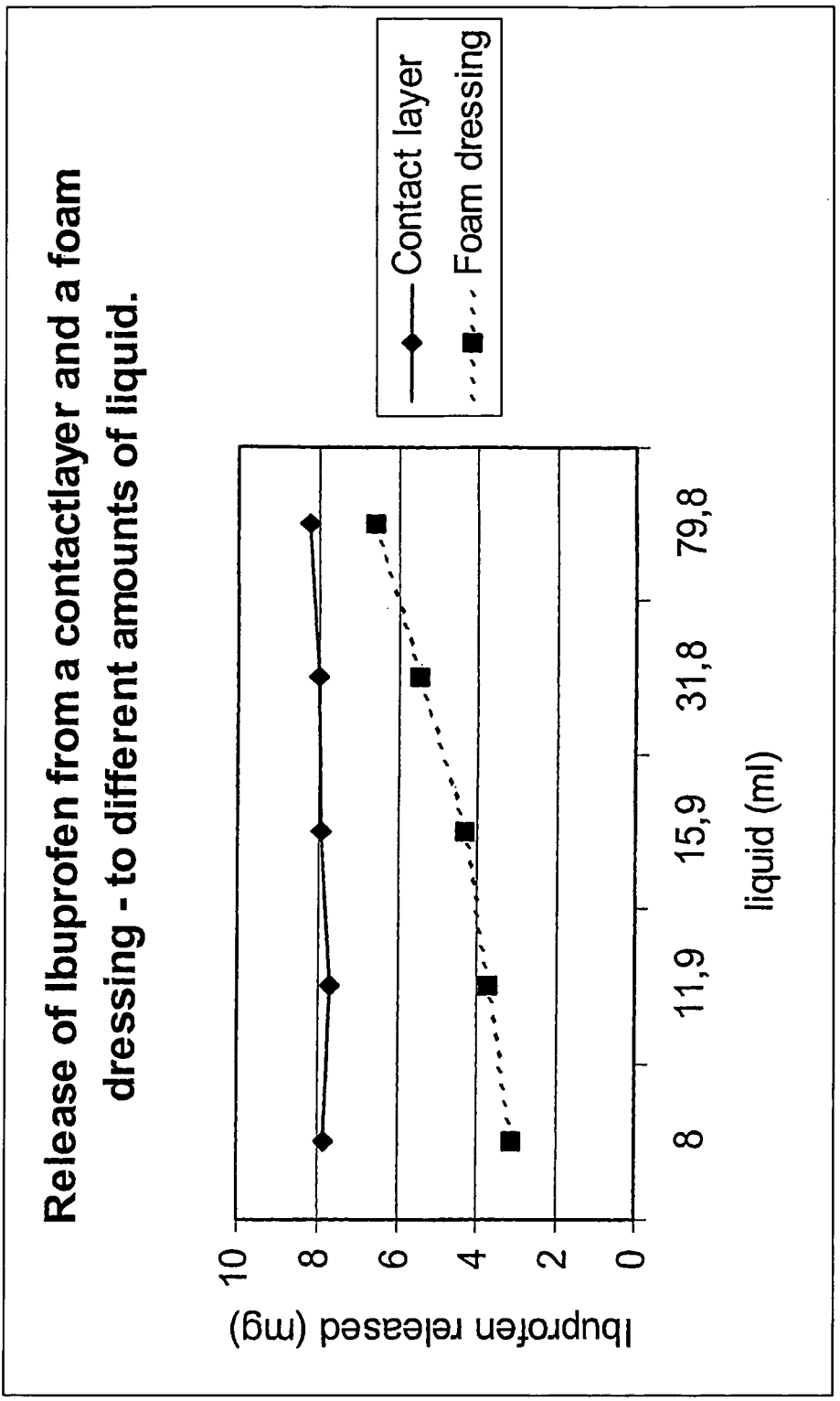
FIG. 2 shows the release of Ibuprofen from a contact layer and a foam dressing.

FIG. 2 shows the release of Ibuprofen from the Vaseline contact layer of Sample A and a foam dressing of Sample B, tested with different amounts of liquid. Both samples contained approximately 8 mg of Ibuprofen, corresponding to a concentration of 0.5 mg/cm$^2$. Release was performed to the following volumes: 8 ml, 11.9 ml, 15.9 ml, 31.8 ml and 79.5 ml. As can be seen from the figure, the release from the contact layer is substantially independent of the amount of liquid used, while the release from the foam dressing increases when the amount of liquid increases. Furthermore, it can be seen that the contact layer released substantially all of the Ibuprofen at the test, while the foam dressing did not release all the Ibuprofen even when exposed to large amounts of liquid.

EXAMPLE 2

A wound-contacting layer comprising a net impregnated with an active substance in Vaseline or PEG base was used for the study. The drug content in each contact layer was 0.05, 0.5 mg or 1 mg drug/cm$^2$ respectively. The contact layers were prepared as shown below.
Vaseline Contact Layer The contact layers were prepared by mixing 85 g Vaseline with 15 g CMC. Ibuprofen was added in different amounts. The mixture was then applied to a polyester net in an amount of approximately 0.02-0.03 g/cm$^2$.
PEG Contact Layer By mixing 60 g low viscosity PEG with 40 g high viscosity PEG and different amounts of ibuprofen PEG contact layers were made. Ibuprofen was added in different amounts. The mixture was then applied a polyester net in an amount of approximately 0.02-0.03 g/cm$^2$.
Method The dressings were cut into circles with a diameter of 4.5 cm and were put into measurement cups with a diameter of 5.5 cm—on a vibrating table. Different amounts of release media (USP phosphate buffer pH 7.4) were added. After 24 hours the release media was analysed for ibuprofen content and the amount of released ibuprofen was calculated.

Figure 3:
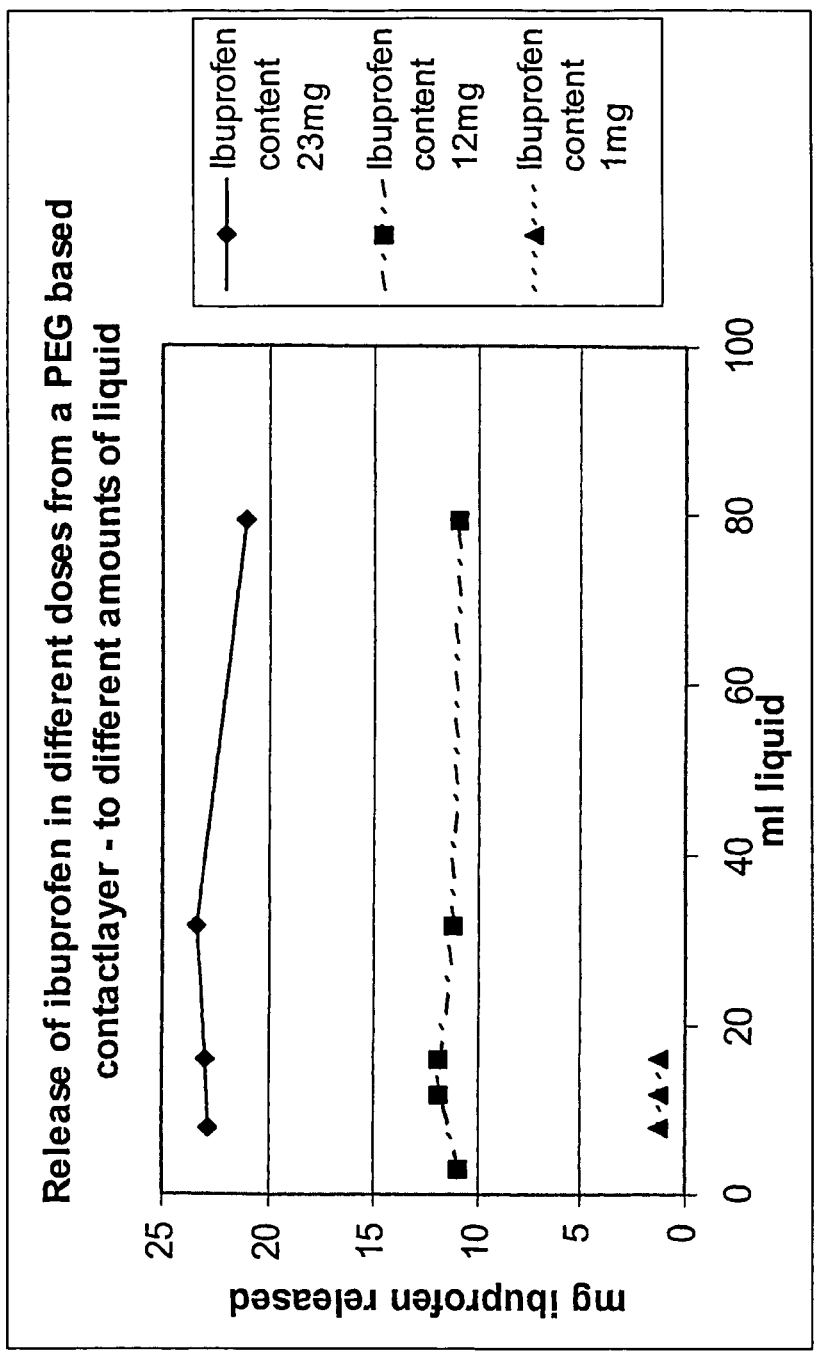
FIG. 3 shows the release of Ibuprofen from a PEG based contact layer.
Figure 4:
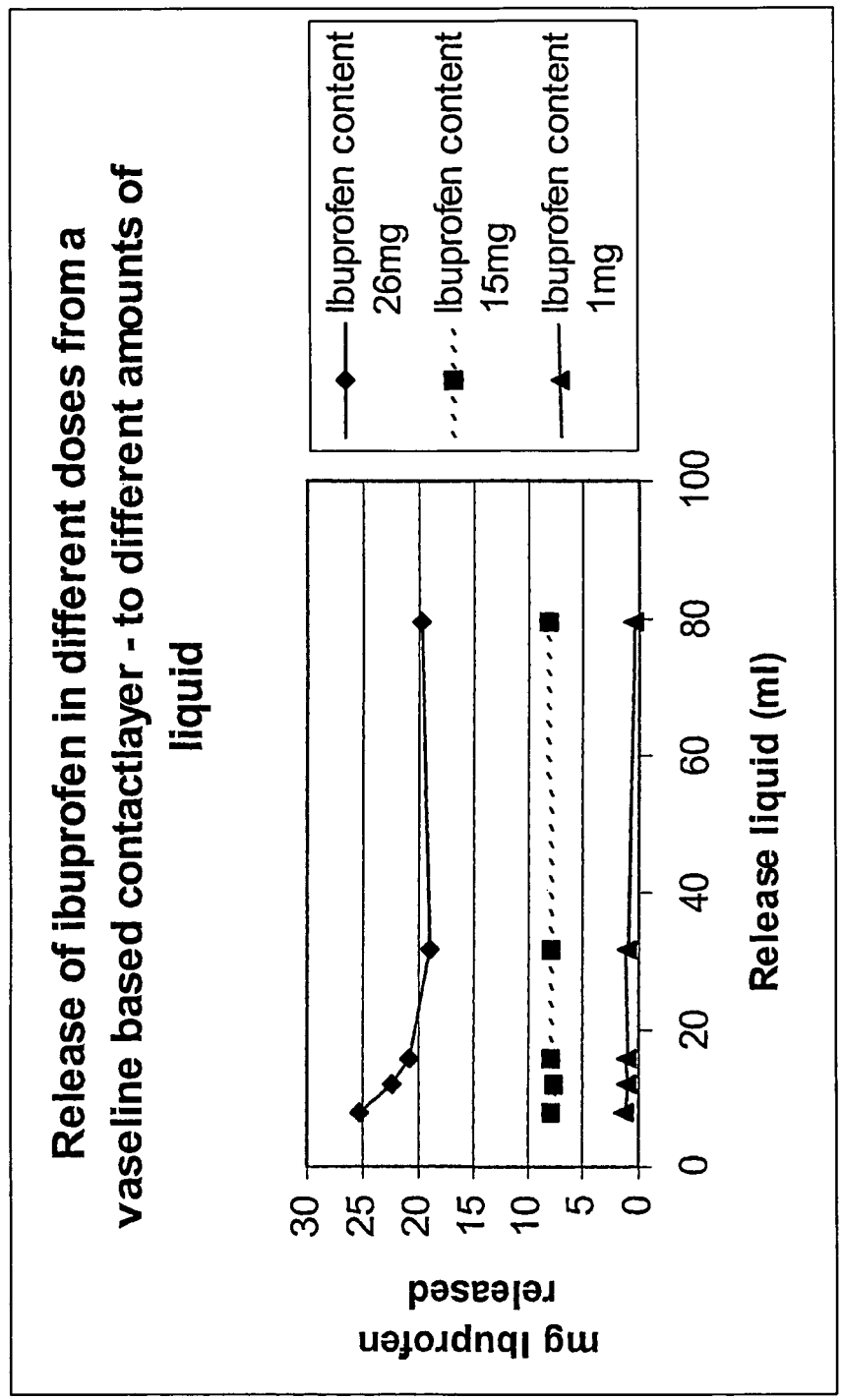
FIG. 4 shows the release of Ibuprofen from a Vaseline based contact layer.

FIG. 3 and FIG. 4 show the release of Ibuprofen from the Vaseline contact layer and the PEG contact layer respectively. The contact layers were tested for three concentrations of Ibuprofen released by different amounts of release liquid. The used concentrations of Ibuprofen were approximately 0.07 mg/cm², 0.7 mg/cm² and 1.4 mg/cm². As can be seen from the figures, the release of the pain-killing agent is substantially independent of the amount of liquid.

The invention claimed is:

1. A wound care device for local treatment of pain in a wound, said device comprising (1) a substantially water-impervious layer or film, (2) a skin-friendly adhesive in which an absorbing constituent or element is incorporated, and (3) a relatively thin wound contacting layer which incorporates a pain killing agent in an amount less than 75% of the systemic daily unit dose for systemic treatment using the agent.

2. The wound care device according to claim 1, wherein the pain-killing agent is an anti-inflammatory pain-killing agent.

3. The wound care device according to claim 1 wherein the pain-killing agent is an NSAID.

4. The wound care device according to claim 3, wherein the pain-killing agent is ibuprofen.

5. The wound care device according to claim 1, wherein the pain-killing agent is incorporated into the wound contacting layer as particles.

6. The wound care device according to claim 5, wherein the particles are incorporated in a film.

7. The wound care device according to claim 1, wherein one or more components are made of a material selected from the group of PVP, PVA, polylactic acids, polysaccharides such as carboxy methyl cellulose (CMC), hydroxymethyl cellulose, chitosan, alginate, or polyacrylic acids, methacrylates, silicones, styrene-isoprene-styrene mixtures, Vaseline, glycols and polyurethane.

8. The wound care device according to claim 1, wherein at least 50% w/w of the pain-killing agent is released during the first 24 hours after application of the wound care device to a wound.

9. The wound care device according to claim 1, wherein at least 50% w/w of the pain-killing agent is released during the first 12 hours after application of the wound care device to a wound.

10. The wound care device according to claim 1, wherein at least 75% w/w of the pain-killing agent is released during the first 24 hours after application of the wound care device to a wound.

11. The wound care device according to claim 1, wherein at least 75% w/w of the pain-killing agent is released during the first 12 hours after application of the wound care device to a wound.

12. The wound care device according to claim 1, wherein at least 75% w/w of the pain-killing agent is released during the first 6 hours after application of the wound care device to a wound.

13. The wound care device according to claim 1, wherein the wound care device has a thickness of less than 1.5 mm.

14. The wound care device according to claim 1, wherein the wound care device has a thickness of less than 1.0 mm.

15. The wound care device according to claim 1, wherein the wound care device has a thickness of less than 0.7 mm.

16. The wound care device according to claim 1, wherein the wound care device has a thickness of less than 0.6 mm.

17. The wound care device according to claim 1, wherein the wound care device has a thickness of less than 0.5 mm.

18. A wound care device for local treatment of pain in a wound, said device comprising (1) a substantially water-impervious layer or film, (2) a skin-friendly adhesive in which an absorbing constituent or element is incorporated, and (3) a relatively thin wound contacting layer incorporating a pain killing agent which is released to the wound so that the plasma concentration of the pain killing agent is below that needed for systemic effect.

19. The wound care device according to claim 7, wherein one or more components are made of a glycol selected from the group consisting of PEG or PEG/PPG mixtures.

* * * * *